US011752237B2

(12) United States Patent
Alsberg et al.

(10) Patent No.: US 11,752,237 B2
(45) Date of Patent: Sep. 12, 2023

(54) BIOACTIVE AGENT SPATIAL PATTERNED BIODEGRADABLE HYDROGELS

(71) Applicant: CASE WESTERN RESERVE UNIVERSITY, Cleveland, OH (US)

(72) Inventors: Eben Alsberg, Cleveland, OH (US); Oju Jeon, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 110 days.

(21) Appl. No.: 16/107,756

(22) Filed: Aug. 21, 2018

(65) Prior Publication Data
US 2019/0054206 A1    Feb. 21, 2019

Related U.S. Application Data

(60) Provisional application No. 62/548,243, filed on Aug. 21, 2017.

(51) Int. Cl.
| A61L 27/20 | (2006.01) |
| A61L 27/54 | (2006.01) |
| A61L 27/44 | (2006.01) |
| A61L 27/36 | (2006.01) |
| A61L 27/52 | (2006.01) |
| A61L 27/58 | (2006.01) |
| C08L 89/06 | (2006.01) |
| C08L 5/04 | (2006.01) |
| C08B 37/00 | (2006.01) |
| C08H 1/06 | (2006.01) |
| A61L 27/26 | (2006.01) |
| A61L 27/38 | (2006.01) |
| C08G 65/00 | (2006.01) |

(52) U.S. Cl.
CPC ............ *A61L 27/44* (2013.01); *A61L 27/20* (2013.01); *A61L 27/26* (2013.01); *A61L 27/3608* (2013.01); *A61L 27/3834* (2013.01); *A61L 27/52* (2013.01); *A61L 27/54* (2013.01); *A61L 27/58* (2013.01); *C08B 37/0084* (2013.01); *C08G 65/002* (2013.01); *C08H 1/06* (2013.01); *C08L 5/04* (2013.01); *C08L 89/06* (2013.01); *A61L 2300/236* (2013.01); *A61L 2300/252* (2013.01); *A61L 2300/412* (2013.01); *A61L 2300/414* (2013.01); *A61L 2400/16* (2013.01); *A61L 2430/40* (2013.01); *C08L 2205/04* (2013.01); *C08L 2312/00* (2013.01)

(58) Field of Classification Search
CPC .... C08L 5/04; C08L 2312/00; C08L 2205/04; A61L 2300/236; A61L 2300/252; A61L 2300/412; A61L 2300/414; A61L 2430/40; A61L 27/20; A61L 27/3608; A61L 27/3834; A61L 27/52; A61L 27/54; A61L 27/58; A61L 27/44; A61L 2400/16; C08B 37/0084; C08B 37/008

See application file for complete search history.

(56) References Cited

U.S. PATENT DOCUMENTS

| 8,388,948 | B2 | 3/2013 | Basu et al. |
| 9,370,606 | B2 | 6/2016 | Nakamura et al. |
| 9,642,914 | B2 | 5/2017 | Alsberg et al. |
| 2008/0226692 | A1 | 9/2008 | Sato et al. |
| 2011/0008443 | A1* | 1/2011 | Alsberg ................. A61K 35/32 424/488 |
| 2016/0279868 | A1 | 9/2016 | Burdick et al. |
| 2017/0327813 | A1 | 11/2017 | Cattolico et al. |

FOREIGN PATENT DOCUMENTS

WO        90/10454 A1    9/1990

OTHER PUBLICATIONS

Samorezov et al. (Bioconjugate Chemistry, 2015, 26, 1339-1347) (Year: 2015).*
Skardal et al. (Tissue Engineering: Part A, vol. 16, No. 8, 2010 2675-2685). (Year: 2010).*
Gomez et al. (Carbohydrate Polymers 67 (2007) 296-304) (Year: 2007).*
Kim, et al., "Independent Control of Topography for 3D Patterning of the ECM Microenvironment", Adv. Mater. 2016, 28, 132-137.
Jeon, et al., "Affinity-based growth factor delivery using biodegradable, photocrosslinked heparin-alginate hydrogels", J Control Release. Sep. 25, 2011; 154(3): 258-266.
Khetan, et al., "Patterning network structure to spatially control cellular remodeling and stem cell fate within 3-dimensional hydrogels", Biomaterials 31 (2010) 8228-8234.
Jabalee, et al., "Vascular endothelial growth factor signaling affects both angiogenesis and osteogenesis during the development of scleral ossicles", Developmental Biology 406(2015)52-62.
Jeon, et al., "Regulation of Stem Cell Fate in a Three-Dimensional Micropatterned Dual-Crosslinked Hydrogel System", Adv Funct Mater. Oct. 11, 2013; 23(38): 4765-4775.
Hynes, et al., "The Extracellular Matrix: Not Just Pretty Fibrils", Nov. 27, 2009 vol. 326.
Gerber, et al., "VEGF regulates haematopoietic stem cell survival by an internal autocrine loop mechanism", Nature, vol. 417, Jun. 27, 2002.

(Continued)

*Primary Examiner* — Anna R Falkowitz
(74) *Attorney, Agent, or Firm* — TAROLLI, SUNDHEIM, COVELL & TUMMINO, LLP

(57) ABSTRACT

A method for forming a bioactive agent spatially patterned includes providing a photocrosslinkable hydrogel that includes a photocrosslinkable base polymer, photocrosslinkable bioactive agent coupling polymer macromers, and at least one bioactive agent that couples to the photocrosslinkable bioactive agent coupling polymer macromer, an selectively exposing discrete portions of the photocrosslinkable hydrogel to actinic radiation effective to initiate crosslinking of the base polymer and the bioactive agent coupling polymer macromers at the exposed portions.

12 Claims, 7 Drawing Sheets

(56) References Cited

OTHER PUBLICATIONS

Hu et al., "Micropatterned Hydrogel Surface with High-Aspect-Ratio Features for Cell Guidance and Tissue Growth", ACS Appl. Mater. Interfaces 2016, 8, 21939-21945.
Deforest, et al., "Dimensional gels", Nature Materials vol. 14, pp. 523-531 (2015).
Frohlich, et al., "Tissue Engineered Bone Grafts: Biological Requirements, Tissue Culture and Clinical Relevance", Curr Stem Cell Res Ther. Dec. 2008; 3(4): 254-264.
Auletta, et al., "Fibroblast Growth Factor-2 Enhances Expansion of Human BoneMarrow-DerivedMesenchymal Stromal Cells without Diminishing Their Immunosuppressive Potential", Stem Cells International, 2011, 1-11.
Deforest, et al., "Photoreversible Patterning of Biomolecules within Click-Based Hydrogels", Angew. Chem. Int. Ed. 2012, 51, 1816-1819.
Applegate, et al., "Laser-based three-dimensional multiscale micropatterning of biocompatible hydrogels for customized tissue engineering scaffolds", vol. 112, Sep. 29, 2015, 12052-12057.
Yu, et al., "TIMP-3 Binds to Sulfated Glycosaminoglycans of the Extracellular Matrix", The Journal of Biological Chemistry, vol. 275, Oct. 6, 2000, 31226-31232.
Aizawa, et al., "Polymers used to influence cell fate in 3D geometry: New trends", Progress in Polymer Science 37 (2012) 645-658.
Lober, et al., "Monolithic Polymers for Cell Cultivation, Differentiation, and Tissue Engineering", Angew. Chem. Int. Ed. 2008, 47, 9138-9141.
Lutolf, et al., "Synthetic biomaterials as instructive extracellular microenvironments for morphogenesis in tissue engineering", Nature Biotechnology, vol. 23, No. 1 Jan. 2005.
Moghaddam, "Significance of vascular endothelial growth factor in growth and peritoneal dissemination of ovarian cancer", Cancer Metastasis Rev (2012) 31:143-162.
Robert M. Nerem, "Tissue Engineering: The Hope, the Hype, and the Future", vol. 12, 2006.
McGann, et al., "Heparin-Functionalized Materials in Tissue Engineering Applications", 2011, Engineering Biomaterials for Regenerative Medicine pp. 225-250.
Nichol, et al., "Cell-laden microengineered gelatin methacrylate hydrogels", Biomaterials. Jul. 2010; 31(21): 5536-5544.
Shah, et al., "Micropatterning of bioactive heparin-based hydrogels", The Royal Society of Chemistry 2010.
Oh, et al., "Differentiation of PC12 cells in three-dimensional collagen sponges with micropatterned nerve growth factor", Biotechnology Progress, vol. 28, Jan. 17, 2012.
Wylie, et al., "Spatially controlled simultaneous patterning of multiple growth factors in three-dimensional hydrogels", Nature Materials, vol. 10, Oct. 2011.
Tacchetti, et al., "Cell condensation in chondrogenic differentiation", Experimental Cell Research, vol. 200, Issue 1, May 1992, pp. 26-33.
Mata, et al., "Micropatterning of bioactive self-assembling gels", Soft Matter, 2009 ; 5(6): 1228-1236.
First Named Inventor: Eben Alsberg; U.S. Appl. No. 16/107,774, filed Aug. 21, 2018; NonFinal Office Action; dated Sep. 17, 2020; 16 pgs.
First Named Inventor: Eben Alsberg; U.S. Appl. No. 16/726,375, filed Dec. 24, 2019; NonFinal Office Action; dated Oct. 5, 2020.
Applicant: Case Western Reserve University; PCT International Application No. PCT/US19/26678; International Filing Date: Apr. 9, 2019; PCT International Search Report and Written Opinion; Authorized Officer: Lee W. Young; Date of Completion: Jun. 11, 2019; 11 pgs.
Applicant: Case Western Reserve University, et al.; European Patent Application No. 17879074.7, Filing Date: Dec. 11, 2017; Communication pursuant to Article 94(3) EPC; dated Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), pp. 4.
Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
Italian Patent Office, Document No. 102011902009885A1, (Bionest LTD), Jul. 1, 2013 (Jul. 1, 2013).
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Rachelle W. Johnson, et al., "Glycoprotein130 (Gp130)/interleukin-6 (IL-6) signalling in osteoclasts promotes bone formation in periosteal and trabecular bone", Bone, vol. 81, Aug. 7, 2015, pp. 343-351.
Rozen, et al., "Fracture repair: Modulation of fracture-callus and mechanical properties by sequential application of IL-6 following PTH 1-34 or PTH 28-48, IL-6 following PTH 1-34 or PTH 28-48", Bone, Pergamon Press., Oxford, GB, vol. 41, No. 3, Aug. 8, 2007, pp. 437-445.
Xin Zhou, et al., "Chondrocytes Transdifferentiate into Osteoblasts in Endochondral Bone during Development, Postnatal Growth and Fracture Healing in Mice", Plos Genetics, vol. 10, No. 12, Dec. 4, 2014.
First Named Inventor: Eben Alsberg; U.S. Appl. No. 16/044,182, filed Jul. 24, 2018; Non-Final Office Action, dated Jun. 24, 2022; 18 pgs.
First Named Inventor: Eben Alsberg; U.S. Appl. No. 16/153,138, filed Oct. 5, 2018; NonFinal Office Action; dated Aug. 12, 2022; 17 pgs.
First Named Inventor: Eben Alsberg; U.S. Appl. No. 16/107,708, filed Aug. 21, 2018; NonFinal Office Action; dated Mar. 3, 2022; 17 pgs.
Kadri, R., et al. "Preparation and characterization of nanofunctionalized alginate/methacrylated gelatin hybrid hydrogels." RSC advances 6.33 (2016): 27879-27884.
First Named Inventor: Eben Alsberg; U.S. Appl. No. 12/191,034, filed Aug. 13, 2008; NonFinal Office Action; dated Oct. 4, 2022; 28 pgs.
First Named Inventor: Eben Alsberg; U.S. Appl. No. 17/544,544, filed Dec. 7, 2021; NonFinal Office Action; dated Dec. 8, 2022; 6 pgs.

* cited by examiner

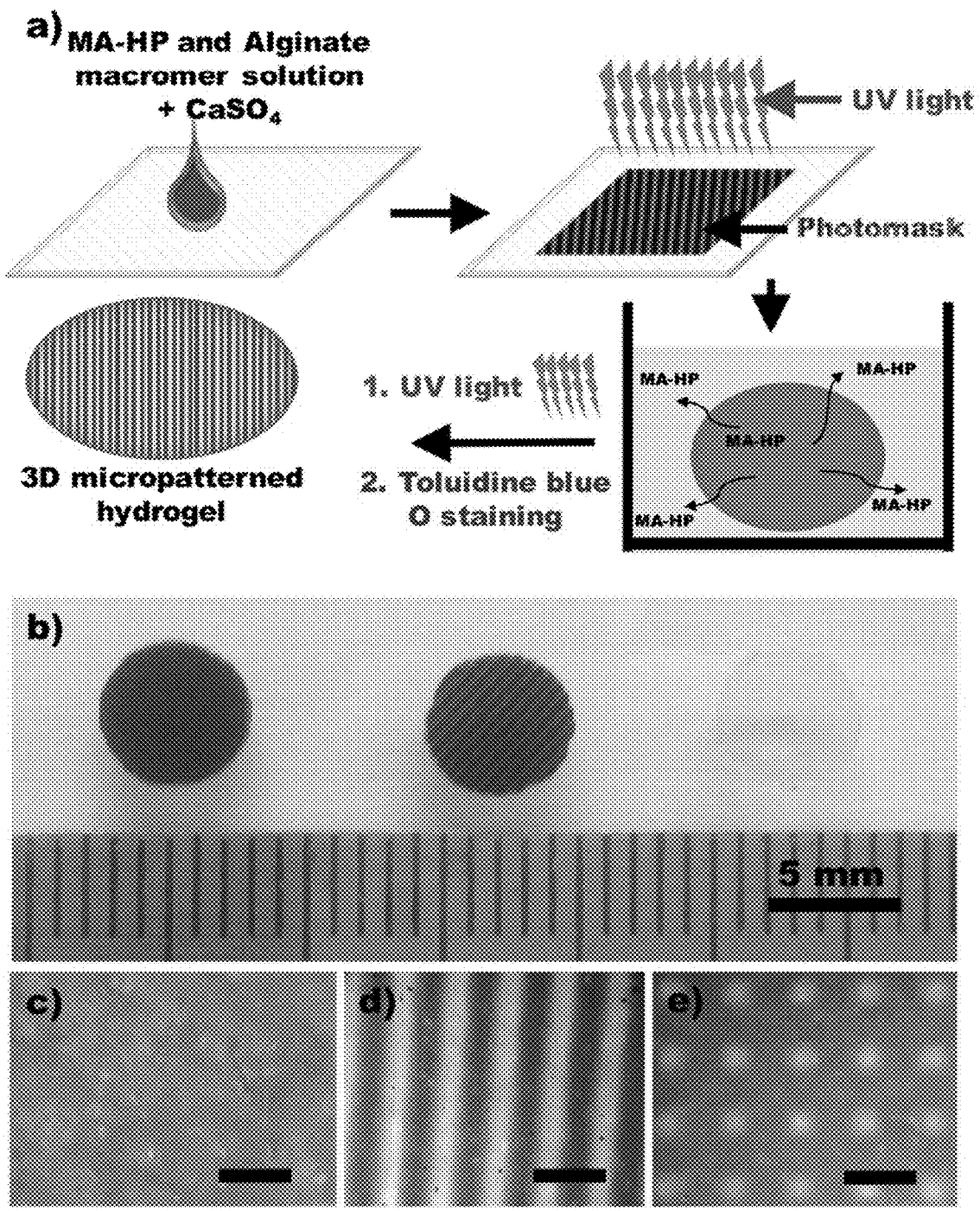
Figs. 1A-E

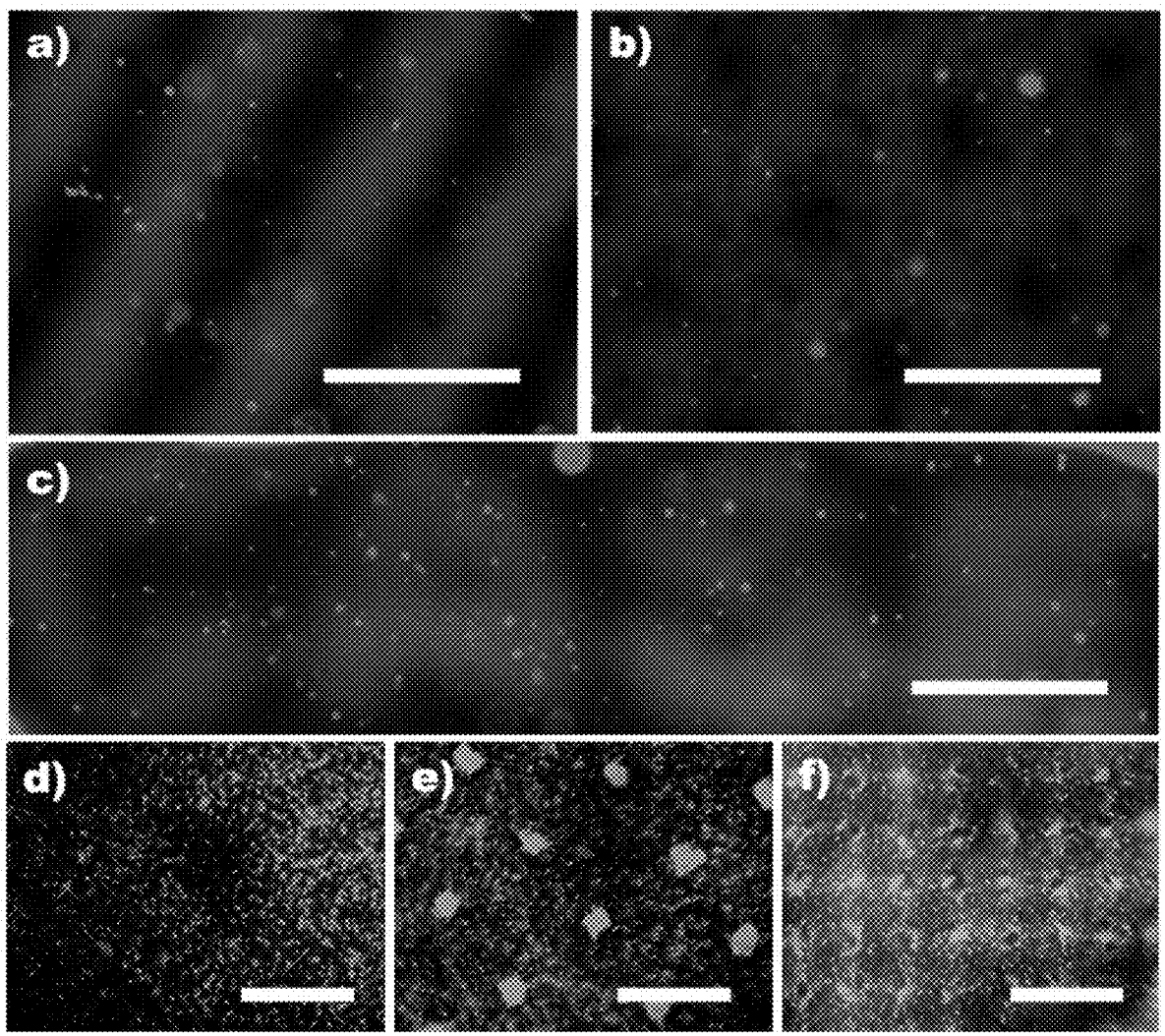
Figs. 2A-F

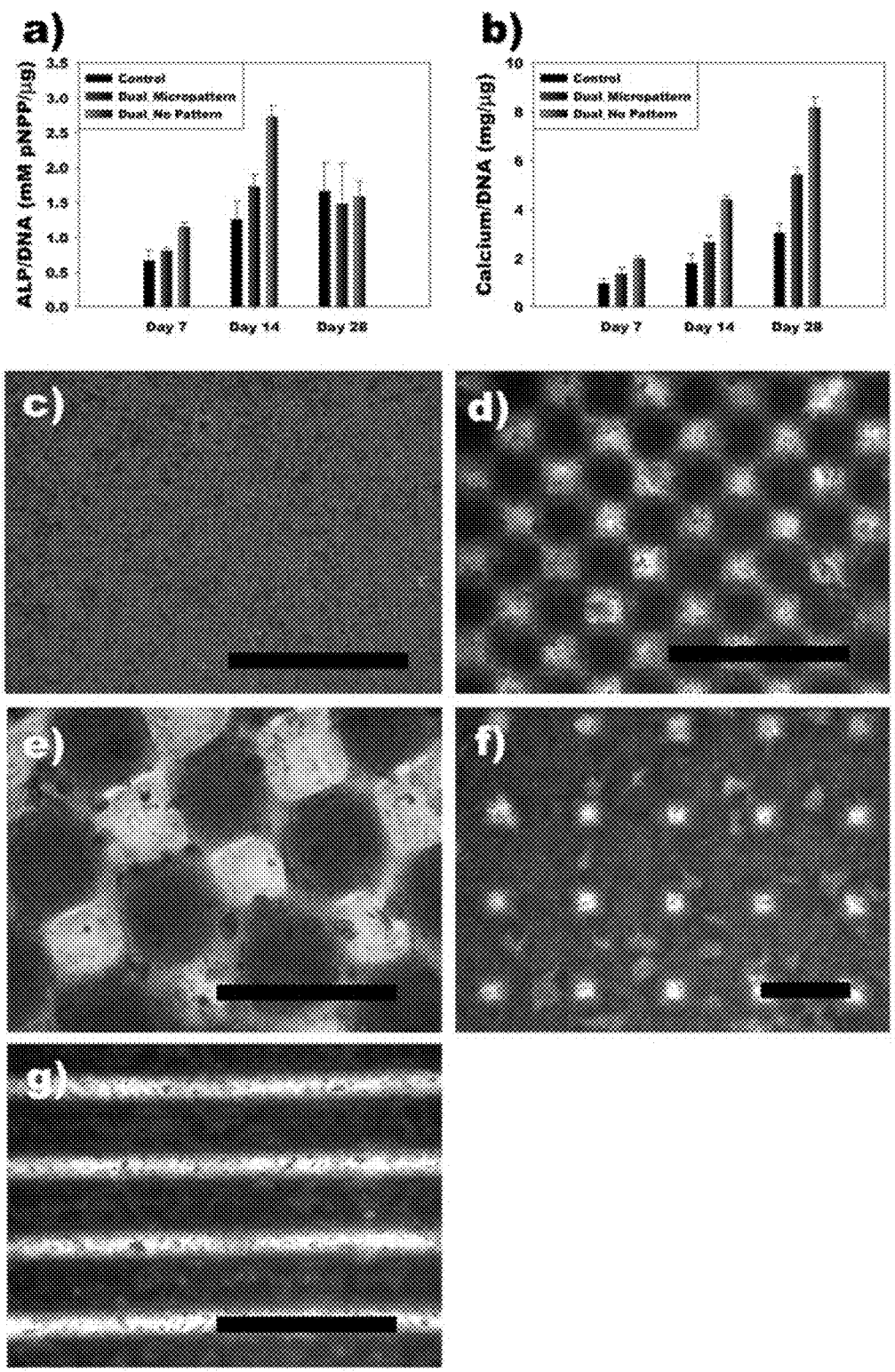
Figs. 3A-G

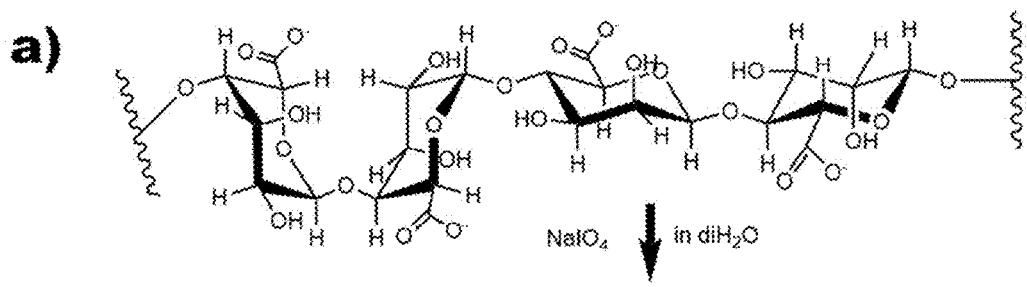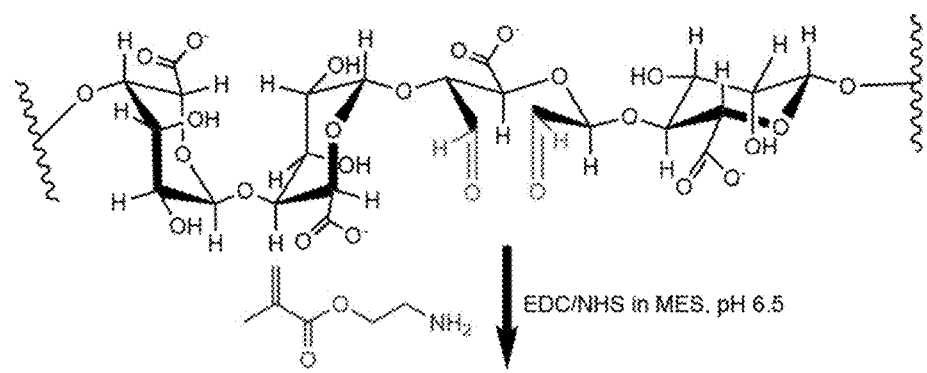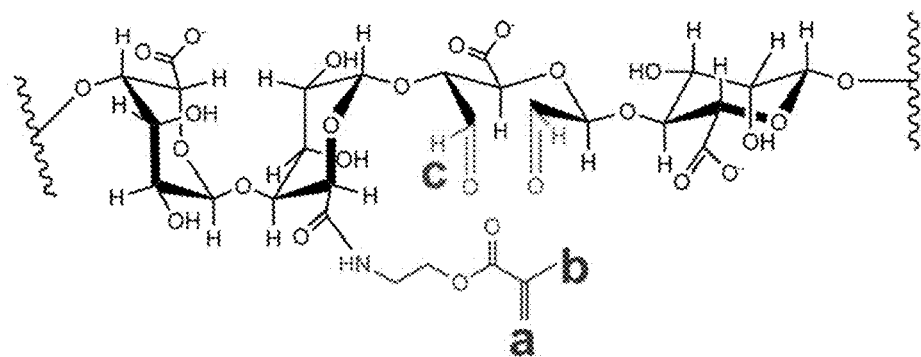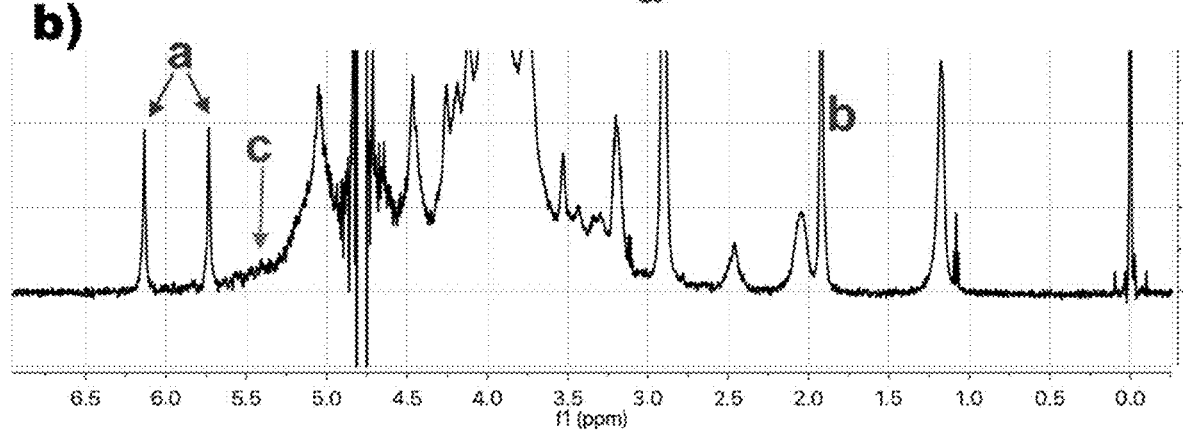
Figs. 4A-B

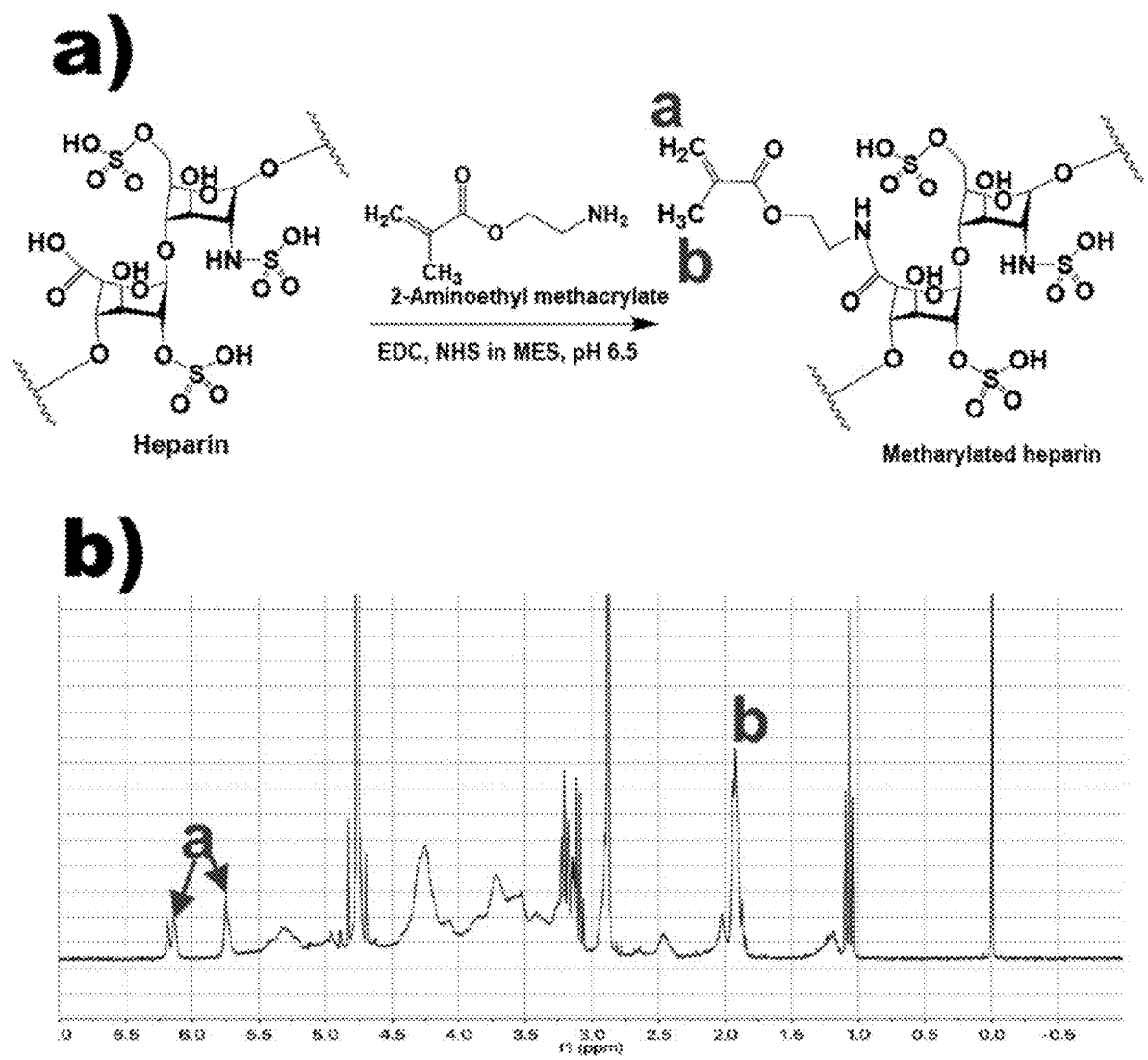
Figs. 5A-B

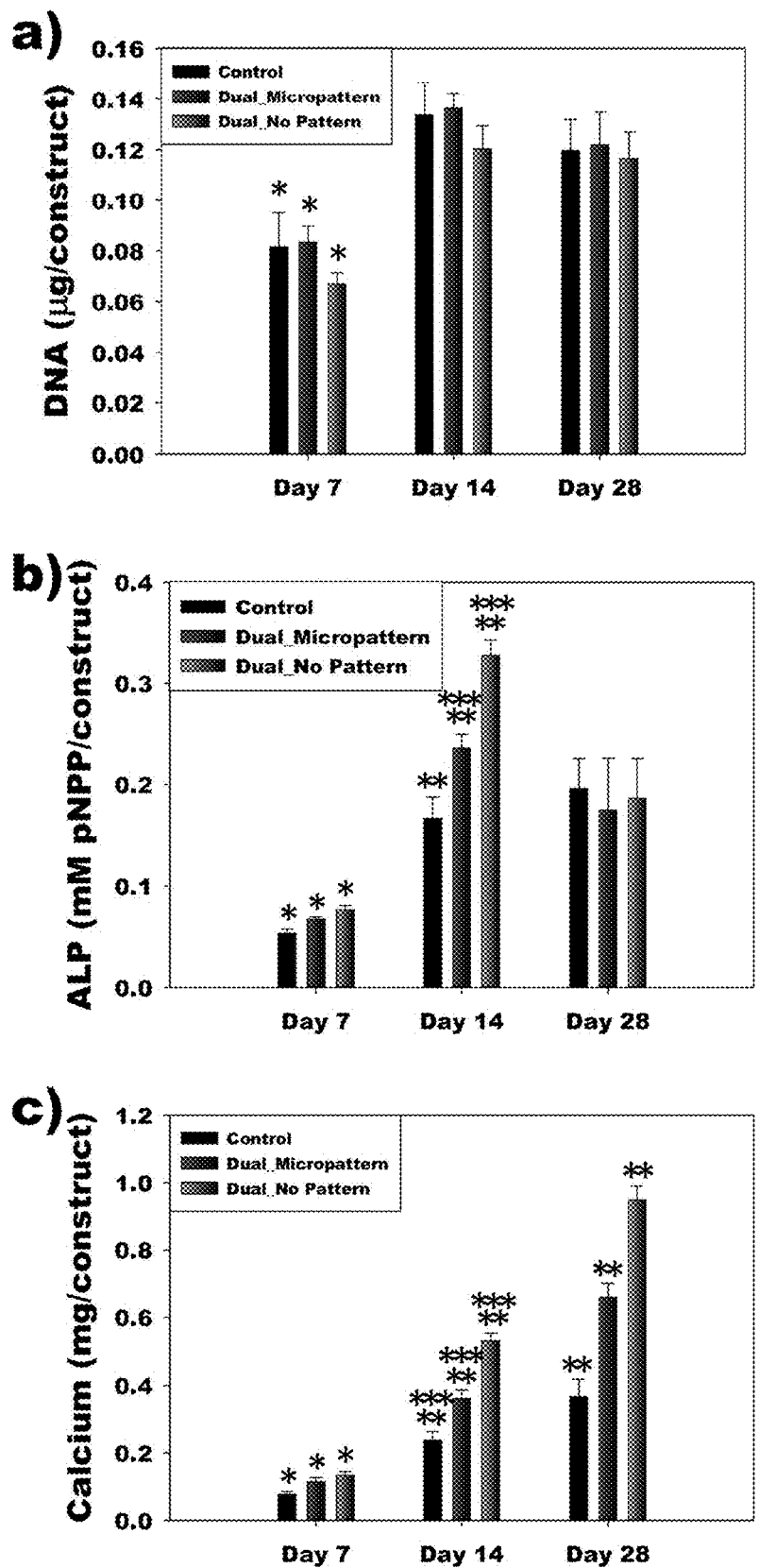
Figs. 7A-C

BIOACTIVE AGENT SPATIAL PATTERNED BIODEGRADABLE HYDROGELS

RELATED APPLICATION

This application claims priority from U.S. Provisional Application No. 62/548,243 filed Aug. 21, 2017, the subject matter of which are incorporated herein by reference in their entirety.

GOVERNMENT FUNDING

This invention was made with government support under AR069564, CA108512, AR066193, AR007505 awarded by the National Institutes of Health. The government has certain rights in the invention.

BACKGROUND

Tissue engineering aims to develop biologically functional substitutes for the purpose of restoring and/or replacing damaged, injured or lost native tissues. One strategy is to incorporate cells within a biomaterial that provides a three-dimensional (3D) microenvironment capable of regulating cell function and ultimately driving new tissue formation. During development and healing processes, cells continuously sense and respond to a variety of biochemical and physical signals from their extracellular microenvironment that play a central role in influencing their behavior, such as migration, growth, survival, apoptosis and differentiation. The temporal and spatial presentation of these signals is critical for the formation of tissues with complex composition and morphology. Thus, the ability to engineer biomaterial systems capable of partially recapitulating the finely orchestrated presentation of these signals both in time and space may permit the mimicking of how these tissues are formed naturally.

Recent progress in micropatterning in biomaterial scaffolds has enabled manipulation of the 3D environment up to the micrometer scale and provided insights in stem cell behavior. For example, a previous study has shown that micropatterning hyaluronic acid hydrogels with degradable peptide-crosslinked regions permitted control over the location of mesenchymal stem cell (MSC) spreading, illustrating its usefulness for regulating stem cell remodeling. In addition, our group has reported that changes in the size of micropatterned regions of a dual-crosslinked alginate hydrogel system with different physical properties had a significant influence on stem cell proliferation and osteogenic and chondrogenic differentiation. Further developments to fabricate micropatterned hydrogels with tailorable physical cues are underway; however, few studies have attempted to construct spatial 3D patterns of growth factors, which are bioactive molecules that are known to play a critical role in the development of tissues.

To date, strategies to engineer 3D micropatterns of growth factors in hydrogels employ sophisticated fabrication procedures that require expertise and expensive equipment and materials, cannot be used to fabricate clinically relevant macro-scale 3D constructs, and/or do not permit simultaneous encapsulate cells.

SUMMARY

Embodiments described herein relate to bioactive agent spatially patterned hydrogels, methods of forming the hydrogels, and to their use in regenerative medicine, cell-based technologies, drug delivery and tissue engineering applications. For example, compositions containing hydrogels described herein can be used as building blocks for tissue engineering as well as for functional implantable objects for cell therapy applications. The hydrogel can optionally include a plurality of cells dispersed therein and be cytocompatible, and, upon degradation, produce substantially non-toxic products. Advantageously, spatiotemporal control over the presentation of bioactive agents within biomaterials, such as the hydrogels described herein, can recapitulate multifaceted and intricate developmental and regenerative processes to drive the engineering of complex tissues.

In some embodiments, a method for forming a bioactive agent spatially patterned hydrogels can include providing a crosslinkable hydrogel that includes a crosslinkable base polymer, crosslinkable bioactive agent coupling polymer macromers, and at least one bioactive agent that couples to the crosslinkable bioactive agent coupling polymer macromer. The hydrogel can also optionally include a photoinitiator and at least one cell dispersed in the hydrogel. Discrete portions of the crosslinkable hydrogel can then be selectively exposed to an activating stimulus (e.g., actinic radiation) effective to initiate cross-linking of the base polymer and the bioactive agent coupling polymer macromers at the exposed portions. The bioactive agent coupling polymer macromers, which are not crosslinked with the base polymer, and optionally, bioactive agent that is not coupled to the crosslinked bioactive agent coupling polymer macromers can then be removed to provide a bioactive agent spatially patterned hydrogel, which includes discrete portions and/or patterns of immobilized bioactive agent. The bioactive agent can be non-covalently coupled to the crosslinked bioactive agent coupling polymer macromers.

In some embodiments, after removing the bioactive agent coupling polymer macromers and optionally bioactive agent that is not coupled to the crosslinked bioactive agent coupling polymer macromers the hydrogel can be exposed to the activating stimulus (e.g., actinic radiation) effective to further cross-link the base polymer and, optionally, the bioactive agent coupling polymer macromers.

In some embodiments, the crosslinkable hydrogel is crosslinked by providing a photomask with a defined pattern and using the photomask to selectively expose the discrete portions of the photocrosslinkable hydrogel to actinic radiation.

In some embodiments, the crosslinkable base polymer can include a plurality of crosslinked acrylated and/or methacrylated natural polymer macromers. The acrylated and/or methacrylated, natural polymer macromers can be polysaccharides, which are optionally oxidized to aldehyde saccharide units. The natural polymer macromers are ionically crosslinkable.

In other embodiments, the bioactive agent coupling polymer macromers can include acrylated and/or methacrylated polymer macromers. Examples of acrylated and/or methacrylated polymer macromers include acrylated and/or methacrylated charged polysaccharides, poly(dimethylamino ethyl methacrylate) (pDMAEMA), poly(dimethylamino ethyl methacrylate-cysteamine) (poly(DMAEMA-co-cys)), acrylated and/or methacrylated linear or branched polyethyleneimine (PEI), and polyethyleneimine-glycidyl methacrylate (PEI-GMA. In one example, the bioactive agent coupling polymer macromer can include heparin and, particularly, acrylated and/or methacrylated heparin.

In some embodiments, the bioactive agent can comprise at least one a polynucleotide, a peptide, or small molecule.

The polynucleotide can include, for example, at least one of DNA fragments, DNA plasmids, or interfering RNA molecules. The peptide can include, for example, a heparin binding growth factor, such as FGF, VEGF, TGF-β, or BMP.

Other embodiments, described herein relate to a method for forming a bioactive agent spatially patterned biodegradable hydrogel. The method can include combining dual crosslinkable natural polymer macromers, which include at least one first photocrosslinkable group, bioactive agent coupling natural polymer macromers, which include at least one second photocrosslinkable group reactive with the first crosslinkable group, and at least one bioactive agent that couples to the bioactive agent coupling natural polymer macromers. A photoinitiator and at least one cell can also be combined with the dual crosslinkable macromer, the bioactive agent coupling natural polymer macromere, and the bioactive agent.

The dual crosslinkable natural polymer macromers can be crosslinked to form a photocrosslinkable hydrogel that includes a photocrosslinkable base polymer, the bioactive agent coupling natural polymer macromers and the at least one bioactive agent.

Discrete portions of the photocrosslinkable hydrogel can then be selectively exposed to actinic radiation effective to initiate cross-linking of the photocrosslinkable base polymer and the bioactive agent coupling polymer macromers at the exposed portions. The bioactive agent coupling polymer macromers, which are not crosslinked with the base polymer, and optionally, bioactive agent that is not coupled to the crosslinked bioactive agent coupling polymer macromers can then be removed to provide a bioactive agent spatially patterned hydrogel, which includes discrete portions and/or patterns of immobilized bioactive agent. The bioactive agent can be non-covalently coupled to the crosslinked bioactive agent coupling polymer macromers.

Still other embodiments relate to a method for forming a growth factor spatially patterned biodegradable hydrogel. The method includes selectively photocros slinking acrylated and/or methacrylated heparin with an acrylate and/or methacrylated alginate hydrogel in the presence of a heparin binding growth factor and optionally cells, to create discrete and/or local patterns of photocrosslinked regions of heparin crosslinked to the alginate hydrogel and removing unreacted acrylated and/or methacrylated heparin and heparin binding growth factor not bound to crosslinked heparin.

In some embodiments, the patterned photocrosslinked region includes immobilized heparin binding growth factor. The heparin binding growth factor can include at least one of FGF, VEGF, TGF-β, or BMP.

BRIEF DESCRIPTION OF THE DRAWINGS

FIGS. 1(A-E) illustrate the fabrication of a heparin micropatterned dual-crosslinked alginate hydrogel. A) Schematic illustration of the preparation of a heparin micropatterned dual-crosslinked alginate hydrogel. B) Photograph of a dual-crosslinked heparin/alginate hydrogel without a micropattern (left), a striped-micropatterned (250 μm) dual-crosslinked heparin/alginate hydrogel, and a dual-crosslinked alginate hydrogel without heparin. Photomicrographs of a Toluidine Blue O stained C) dual-crosslinked heparin/alginate hydrogel without a micropattern, D) stripe-micropatterned (250 μm) hydrogel and E) grid-micropatterned (200 μm) dual-crosslinked heparin/alginate hydrogel.

FIGS. 2(A-F) illustrate the formation of growth factor micropatterned dual-crosslinked alginate hydrogels and local promotion of hMSC clustering. Fluorescence photomicrographs of A) stripe (250 μm), B) grid (200 μm) C) letters (250 μm, CASE) of VEGF micropatterned, dual-crosslinked alginate hydrogels stained with VEGF antibody. Representative Live (FDA, green)/Dead (EB, red) photomicrographs of hMSCs encapsulated in D) grid (200 μm) micropatterned dual-crosslinked heparin/alginate hydrogels without FGF-2 and E) square (50 μm×50 μm) and F) checkerboard (100 μm) micropatterned FGF-2 in dual-crosslinked heparin/alginate hydrogels after 28 days culture in vitro. All scale bars indicate 250 μm.

FIGS. 3(A-G) illustrate encapsulation of hMSCs in BMP-2 micropatterned dual-crosslinked alginate hydrogels induces micropatterned hMSC osteogenesis. Quantification of A) ALP/DNA and B) Calcium/DNA produced by hMSCs encapsulated within a dual-crosslinked heparin/alginate hydrogel without BMP-2 (Control), a checkerboard micropattern (200 μm) of BMP-2 in a dual-crosslinked heparin/alginate hydrogel (Dual_Micropattern), and a BMP-2-loaded dual-crosslinked heparin/alginate hydrogel without a micropattern (Dual_No Pattern). *$p<0.05$ compared to other groups at a specific time point. **$p<0.05$ compared to other time points within a specific group. Optical photomicrographs of mineralization of hMSCs encapsulated in C) Dual_No Pattern and micropatterned D-E) checkerboards (100 and 200 μm), f) a grid (200 μm) and g) stripes (250 μm) of BMP-2 micropatterned hydrogels after 28 days culture in osteogenic differentiation media. All scale bars indicate 400 μm.

FIGS. 4(A-B) A) schematically illustrate the preparation of OMA and B) the $^1$H-NMR spectrum of the material.

FIGS. 5(A-B) A) schematically illustrate the preparation of methacrylated heparin and B) the $^1$H-NMR spectrum of the material.

FIGS. 7(A-C) illustrate graphs showing the quantification of A) ALP, B) Calcium, and C) DNA in hydrogels composed of hMSCs encapsulated within dual-crosslinked heparin/alginate hydrogel without BMP-2 (Control), checkerboards (200 μm) of BMP-2 micropatterned dual-crosslinked heparin/alginate hydrogel (Dual_Micropattern), and BMP-2-loaded dual-crosslinked heparin/alginate hydrogel without micropattern (Dual_No Pattern). *$p<0.05$ compared to Days 14 and 28 within a specific group. $p<0.05$ compared to the other groups at a specific time point. *$p<0.05$ compared to Day 28 within a specific group.

DETAILED DESCRIPTION

Figure 6:
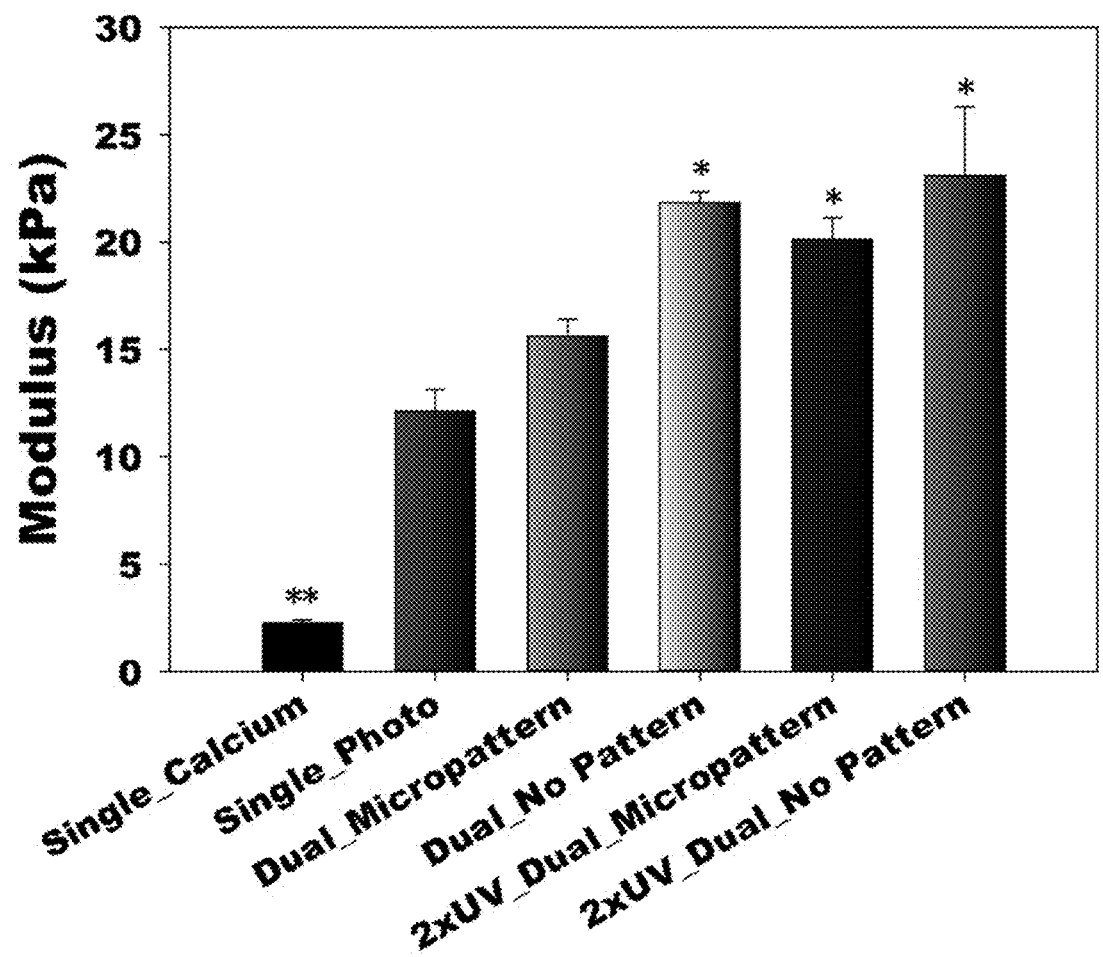
FIG. 6 illustrates a graph showing moduli of single-crosslinked heparin/alginate hydrogels by calcium and UV, micropatterned dual-crosslinked heparin/alginate hydrogel (Dual_Micropattern), dual-crosslinked heparin/alginate hydrogel without pattern (Dual_No Pattern), and dual-crosslinked heparin/alginate hydrogels (2×UV_Dual_Micropattern and 2×UV_Dual_No Pattern), which are further crosslinked under UV light at ~20 mW/cm² for 1 min after removing the unreacted methacrylated heparin from the micropatterned hydrogel by incubating in DMEM containing 0.05 w/v % photoinitiator for 1 hr. *$p<0.05$ compared to Single_Calcium, Single_Photo and Dual_Micropattern groups. **$p<0.05$ compared to Single_Photo and Dual_Micropattern groups.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "bioactive agent" can refer to any agent capable of promoting tissue growth, inhibition, formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

The term "gel" includes gels and hydrogels.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "population" can refer to a collection of cells, such as a collection of progenitor and/or differentiated cells.

As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage.

Embodiments described herein relate to bioactive agent spatially patterned hydrogels, methods of forming the hydrogels, and to their use in regenerative medicine, cell-based technologies, drug delivery and tissue engineering applications. For example, compositions containing hydrogels described herein can be used as building blocks for tissue engineering as well as for functional implantable objects for cell therapy applications. The hydrogel can optionally include a plurality of cells dispersed therein and be cytocompatible, and, upon degradation, produce substantially non-toxic products. Advantageously, spatiotemporal control over the presentation of bioactive agents within biomaterials, such as the hydrogels described herein, can recapitulate multifaceted and intricate developmental and regenerative processes to drive the engineering of complex tissues.

The bioactive agent spatially patterned hydrogels can be substantially cytocompatible (i.e., substantially non-cytotoxic) and includes controllable physical properties, such as degradation rate, swelling behavior, and mechanical properties.

The bioactive agent spatially patterned hydrogels can include a base polymer that is crosslinked with a plurality of bioactive agent coupling polymer macromers at discrete portions and/or patterns of the hydrogel. At least one bioactive agent can be coupled to the crosslinked bioactive agent coupling polymer macromers to provide discrete portions and/or patterns of immobilized bioactive agent. The bioactive agent can be non-covalently coupled to the crosslinked bioactive agent coupling polymer macromers.

In some embodiments, the base polymer can include a crosslinkable hydrogel forming natural polymer macromer that can be potentially crosslinked to form a crosslinkable hydrogel. The natural polymer macromers can potentially be crosslinked by actinic radiation (e.g., photocrosslinkable) or crosslinkable using other means (e.g., thermal, acoustic, magnetic, etc.)

The natural polymer macromers can be any crosslinkable natural polymer or oligomer that includes a functional group (e.g., an acrylate group and/or methacrylate group) that can be further polymerized. Examples of natural polymers or oligomers are saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose.

In some embodiments, the natural polymer macromers can include acrylated and/or methacrylated natural polymer macromers. Acrylated and/or methacrylated natural polymer macromers can include saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose that can be readily oxidized to form free aldehyde units.

In some embodiments, the acrylated or methacrylated, natural polymer macromers are polysaccharides, which are optionally oxidized so that up to about 50% of the saccharide units therein are converted to aldehyde saccharide units.

Control over the degree of oxidation of the natural polymer macromers permits regulation of the gelling time used to form the hydrogel as well as the mechanical properties, which allows for tailoring of these mechanical properties depending on the clinical application.

In other embodiments, acrylated and/or methacrylated, natural polymer macromers can include oxidized, acrylated or methacrylated, alginates, which are optionally oxidized so that up to about 50% of the saccharide units therein are converted to aldehyde saccharide units. Natural source alginates, for example, from seaweed or bacteria, are useful and can be selected to provide side chains with appropriate M (mannuronate) and G (guluronate) units for the ultimate use of the polymer. Alginate materials can be selected with high guluronate content since the guluronate units, as opposed to the mannuronate units, more readily provide sites for oxidation and crosslinking. Isolation of alginate chains from natural sources can be conducted by conventional methods. See Biomaterials: Novel Materials from Biological Sources, ed. Byrum, Alginates chapter (ed. Sutherland), p. 309-331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in Spaltro (U.S. Pat. No. 5,490,978) with other alcohols such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the natural polymer macromers (e.g., alginate material) can be performed using a periodate oxidation agent, such as sodium periodate, to provide at least some of the saccharide units of the natural polymer macromer with aldehyde groups. The degree of oxidation is controllable by the mole equivalent of oxidation agent, e.g., periodate, to saccharide unit. For example, using sodium periodate in an equivalent % of from 2% to 100%, preferably 1% to 50%, a resulting degree of oxidation, i.e., % if saccharide units converted to aldehyde saccharide units, from about 2% to 50% can be obtained. The aldehyde groups provide functional sites for crosslinking and for bonding tissue, cells, prosthetics, grafts, and other material that is desired to be adhered. Further, oxidation of the natural polymer macromer facilitates their degradation in vivo, even if they are not lowered in molecular weight. Thus, high molecular weight alginates, e.g., of up to 300,000 daltons, may be degradeable in vivo, when sufficiently oxidized, i.e., preferably at least 5% of the saccharide units are oxidized.

In some embodiments, the natural polymer macromer (e.g., alginate) can be acrylated or methacrylated by reacting an acryl group or methacryl with a natural polymer or oligomer to form the oxidized, acrylated or methacrylated natural polymer macromer (e.g., alginate). For example, oxidized alginate can be dissolved in a solution chemically functionalized with N-hydroxysuccinimide and 1-ethyl-3-(3-dimethylaminopropyl)-carbodiimide hydrochloride to activate the carboxylic acids of alginate and then reacted with 2-aminoethylmethacrylate to provide a plurality of methacrylate groups on the alginate.

The degree of acrylation or methacrylation can be controlled to control the degree of subsequent crosslinking of the acrylate and methacrylates as well as the mechanical properties, and biodegradation rate of the composition. The degree of acrylation or methacrylation can be about 1% to about 50%, although this ratio can vary more or less depending on the end use of the composition.

The bioactive agent coupling polymer macromers that are crosslinked with the base polymer used to form the hydrogel at discrete portions and/or patterns can include any polymeric molecule that can complex (electrostatically couple) or bind with and/or to the bioactive agent and crosslink with the base polymer.

In some embodiments, the bioactive agent coupling polymer macromers can include acrylated and/or methacrylated polymer macromers, which are photocrosslinkable, crosslinkable base polymer. Examples of acrylated and/or methacrylated polymer macromers include acrylated and/or methacrylated charged polysaccharides, poly(dimethylamino ethyl methacrylate) (pDMAEMA), poly(dimethylamino ethyl methacrylate-cysteamine) (poly(DMAEMA-co-cys)), acrylated and/or methacrylated linear or branched polyethyleneimine (PEI), and polyethyleneimine-glycidyl methacrylate (PEI-GMA. In one example, the bioactive agent coupling polymer macromer can include heparin and, particularly, acrylated and/or methacrylated heparin.

The at least one bioactive agent coupled to the bioactive agent coupling polymer macromers can include any agent capable of modulating a function and/or characteristic of a cell that is dispersed on or within the photocrosslinked biodegradable hydrogel. Alternatively or additionally, the bioactive agent may be capable of modulating a function and/or characteristic of an endogenous cell surrounding a photocrosslinked biodegradable hydrogel implanted in a tissue defect, for example, and guide the cell into the defect.

Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

In some embodiments, where the bioactive agent coupling polymer macromers include heparin, the bioactive agent can be a heparin binding growth factor. The heparin binding growth factor can include, for example, FGF, VEGF, TGF-β, or BMP.

In other embodiments, where the bioactive agent coupling polymer includes a cationic polymer, such as polyethyleneimine, the bioactive can be a polynucleotide, such as an interfering RNA molecule. The interfering RNA molecule can include any RNA molecule that is capable of silencing a target mRNA and thereby reducing or inhibiting expression of a polypeptide encoded by the target mRNA. Alternatively, the interfering RNA molecule can include a DNA molecule encoding for a shRNA of interest. For example, the interfering RNA molecule can comprise a short interfering RNA (siRNA) or microRNA molecule capable of silencing a target mRNA that encodes any one or combination of the polypeptides or proteins.

In some embodiments, the bioactive agent spatially patterned hydrogels can include at least one cell dispersed on or within the hydrogel. For example, cells can be entirely or partly encapsulated within the bioactive agent spatially patterned hydrogels. Cells can include any progenitor cell, such as a totipotent stem cell, a pluripotent stem cell, or a multipotent stem cell, as well as any of their lineage descendant cells, including more differentiated cells (described above), such as MSCs.

The cells can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into or onto the biodegradable hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

Generally, cells can be introduced into the bioactive agent spatially patterned hydrogels in vitro, although in vivo seeding approaches can optionally or additionally be employed. Cells may be mixed with the macromers used to form the bioactive agent spatially patterned hydrogels and cultured in an adequate growth (or storage) medium to ensure cell viability. If the biodegradable hydrogel is to be implanted for use in vivo after in vitro seeding, for example, sufficient growth medium may be supplied to ensure cell viability during in vitro culture prior to in vivo application. Once the bioactive agent spatially patterned hydrogels has been implanted, the nutritional requirements of the cells can be met by the circulating fluids of the host subject.

Any available method may be employed to introduce the cells into the bioactive agent spatially patterned hydrogels. For example, cells may be injected into the bioactive agent spatially patterned hydrogels (e.g., in combination with growth medium) or may be introduced by other means, such as pressure, vacuum, osmosis, or manual mixing. Alternatively or additionally, cells may be layered on the bioactive agent spatially patterned hydrogels, or the bioactive agent spatially patterned hydrogels may be dipped into a cell suspension and allowed to remain there under conditions and for a time sufficient for the cells to incorporate within or attach to the hydrogel. Generally, it is desirable to avoid excessive manual manipulation of the cells in order to minimize cell death during the impregnation procedure. For example, in some situations it may not be desirable to manually mix or knead the cells with the bioactive agent spatially patterned hydrogels; however, such an approach may be useful in those cases in which a sufficient number of cells will survive the procedure. Cells can also be introduced into the bioactive agent spatially patterned hydrogels in vivo simply by placing the hydrogel in the subject adjacent a source of desired cells. Bioactive agents released from the bioactive agent spatially patterned hydrogels may also recruit local cells, cells in the circulation, or cells at a distance from the implantation or injection site.

As those of ordinary skill in the art will appreciate, the number of cells to be introduced into the bioactive agent spatially patterned hydrogels will vary based on the intended application of the hydrogel and on the type of cell used. Where dividing autologous cells are being introduced by injection or mixing into the biodegradable hydrogel, for example, a lower number of cells can be used. Alternatively, where non-dividing cells are being introduced by injection or mixing into the biodegradable hydrogel, a larger number of cells may be required. It should also be appreciated that the macromer scaffold can be in either a hydrated or lyophilized state prior to the addition of cells. For example, the macromer scaffold can be in a lyophilized state before the addition of cells is done to re-hydrate and populate the scaffold with cells.

In other embodiments, the bioactive agent spatially patterned hydrogels can include at least one attachment molecule to facilitate attachment of at least one cell thereto. The attachment molecule can include a polypeptide or small molecule, for example, and may be chemically immobilized onto the biodegradable hydrogel to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences.

Other embodiments described herein relate to a method of forming bioactive agent spatially patterned hydrogels. The method can include providing a crosslinkable hydrogel that includes a crosslinkable base polymer, crosslinkable bioactive agent coupling polymer macromers, and at least one bioactive agent that couples to the crosslinkable bioactive agent coupling polymer macromer. The hydrogel can also optionally include at least one cell dispersed in the hydrogel as well as means to initiate crosslinking of the crosslinkable hydrogel and the crosslinkable bioactive agent coupling polymer.

In some embodiments, the crosslinkable base polymer and crosslinkable bioactive agent coupling polymer macromers can include a photocrosslinkable base polymer and a photocrosslinkable bioactive agent coupling polymer macromer. A photoinitiator can be provided in a photocrosslinkable hydrogel composition to initiate crosslinking of the photocrosslinkable base polymer and the photocrosslinkable bioactive agent coupling polymer macromer. Examples of the photoinitiator can include camphorquinone, benzoin methyl ether, 2-hydroxy-2-methyl-1-phenyl-1-propanone, diphenyl(2,4,6-trimethylbenzoyl)phosphine oxide, benzoin ethyl ether, benzophenone, 9,10-anthraquinone, ethyl-4-N, N-dimethylaminobenzoate, diphenyliodonium chloride and derivatives thereof.

Discrete portions of the photocrosslinkable hydrogel can then be selectively exposed to activating stimulus effective to initiate cross-linking of the base polymer and the bioactive agent coupling polymer macromers at the exposed portions. In some embodiments, the activating stimulus can include actinic or thermal radiation. In other embodiment, the activating stimulus can include magnetic or acoustic energy that facilitates cross-linking at the exposed portions.

The bioactive agent coupling polymer macromers, which are not crosslinked with the base polymer, and optionally, bioactive agent that is not coupled to the crosslinked bioactive agent coupling polymer macromers can then be removed to provide a bioactive agent spatially patterned hydrogel, which includes discrete portions and/or patterns of immobilized bioactive agent. The bioactive agent can be non-covalently coupled to the crosslinked bioactive agent coupling polymer macromers.

In some embodiments, after removing the bioactive agent coupling polymer macromers and optionally bioactive agent that is not coupled to the crosslinked bioactive agent coupling polymer macromers the hydrogel can be exposed to activating stimulus effective to further cross-link the base polymer and, optionally, the bioactive agent coupling polymer macromers.

In some embodiments, the hydrogel can be crosslinked by selectively exposing the hydrogel to actinic radiation. In one example, a photomask can be provided with a defined pattern and that allows the actinic radiation to be transmitted or shine through the photomask in a defined pattern on the hydrogel. In another example, discrete portions of the hydrogel can be selectively exposed to actinic radiation using a multiphoton radiation source, such as two-photon radiation source that provides actinic radiation at discrete portions of the hydrogel.

FIG. 1 illustrates an example of a method of forming a bioactive agent spatially patterned hydrogel that includes a plurality of methacrylated alginate macromers photocrosslinked with a plurality of methacrylated heparin macromers. In the method, oxidized methacrylated alginate, methacrylated heparin can be dissolved in Dulbecco's Modified Eagle Medium (DMEM, Sigma, St. Louis, Mo.) with 0.05 w/v % photoinitiator and the a growth factor (e.g., TGF-β1, bFGF, VEGF or BMP-2). Macromer solution can then be combined or mixed with an aqueous ionic crosslinking solution of calcium sulfate. The two solutions upon mixing can be placed between quartz (top) and glass (bottom) plates separated spacers, and allowed to form an ionically crosslinked hydrogel at room temperature. Subsequently, a photomask with various patterns can be placed on top of the quartz plate, and a micropatterned dual-crosslinked hydrogel formed by exposure to UV light (320-500 nm, EXFO OmniCure S1000-1B, Lumen Dynamics Group) at ~20 mW/cm2 through the photomask for 1 min. The unreacted methacrylated heparin from the micropatterned hydrogel and growth factor can be removed by washing the hydrogel in DMEM containing 0.05 w/v % photoinitiator for 1 hr. To minimize any potential mechanical property differences between the single- and dual-crosslinked regions, micropatterned dual-crosslinked hydrogels can then further photocrosslinked under UV light, e.g., at ~20 mW/cm$^2$ for 1 min, without a photomask to crosslink the methacrylate groups of alginate in the originally single-crosslinked regions.

It should also be appreciated that the bioactive agent spatially patterned hydrogels can be formed with at least one cell. For example, a plurality of cells may be dispersed in a substantially uniform manner on or within the hydrogel or, alternatively, dispersed such that different densities and/or spatial distributions of different or the same cells are dispersed within different portions of the hydrogel. The cells can be autologous, allogeneic or xenogeneic. It will also be appreciated that the cells may be seeded before or after the macromers are crosslinked. Alternatively, crosslinked hydrogels can be incubated in a solution of at least one bioactive agent after the macromers are cross-linked.

The bioactive agent spatially patterned hydrogels can be used in a variety of biomedical applications, including tissue engineering, drug discovery applications, and regenerative medicine. In one example, a bioactive agent spatially patterned hydrogels can be used to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the bioactive agent spatially patterned hydrogel can be administered to the target site. The hydrogel can be prepared according to the method described above. For example, a plurality of cells, such as chondrocytes may be mixed with a plurality of methacrylated alginate macromers and methacrylated heparin macromers to form a solution. The solution may also be mixed with at least one attachment molecule, such as an acrylated or methacrylated polypeptide. For example, this step can be carried out if the at least one attachment molecule is mixed with an acrylated or methacrylated solution prior to crosslinking. Otherwise, the at least one attachment molecule can be previously bound to the alginate macromers using carbodiimide chemistry, for example. Chondrocytes may be obtained from a host subject and then expanded to a desired density ex vivo.

Next, the bioactive agent spatially patterned hydrogel may be loaded into a syringe or other similar device and injected or implanted into the tissue defect. Upon injection or implantation into the tissue defect, the biodegradable hydrogel be formed into the shape of the tissue defect using tactile means.

After implanting the bioactive agent spatially patterned hydrogel into the subject, the chondrocytes can begin to migrate from the hydrogel into the tissue defect, express growth and/or differentiation factors, and/or promote chondroprogenitor cell expansion and differentiation. Additionally, the presence of the bioactive agent spatially patterned hydrogel in the tissue defect may promote migration of endogenous cells surrounding the tissue defect into the bioactive agent spatially patterned hydrogel.

Advantageously, the bioactive agent spatially patterned hydrogels can allow for substantially more uniform spatial delivery of the bioactive agent throughout the interior of the hydrogel. The substantially uniform distribution of the bioactive agent spatially patterned hydrogels and relatively uniform release of the bioactive agent is advantageous for several reasons, including, but not limited to: (1) rapidly inducing uniform cell differentiation; (2) reducing or eliminating in vitro culture of aggregates prior to utilization in in vivo regeneration strategies; (3) providing control over the spatiotemporal presentation of growth factors; and (4) allowing for the use of lower concentrations of growth factors as compared to systems employing exogenously-supplied growth factors.

The following example is for the purpose of illustration only and is not intended to limit the scope of the claims, which are appended hereto.

Example 1

In this Example we developed a simple, cheap and cytocompatible but robust 3D growth factor-micropatterned hydrogel system by photofunctionalization of methacrylated heparin into dual-crosslinkable alginate hydrogels, and use it to evaluate the effect of micropatterned growth factors on encapsulated stem cell behavior. Alginate was oxidized and methacrylated (FIG. 4) to form biodegradable, dual-crosslinkable hydrogels by ionic crosslinking with calcium ions ($Ca^{2+}$) and photocrosslinking under ultraviolet (UV) light (FIG. 1A). To incorporate and micropattern the heparin into the dual-crosslinkable alginate hydrogels during the photopolymerization process, methacrylate groups were covalently coupled to the heparin backbone by reacting the carboxylic acid groups of the heparin with the amine groups of 2-aminoethyl methacrylates using standard carbodiimide chemistry (FIG. 5). The overall strategy for the formation of 3D heparin-micropatterned hydrogels is depicted in FIG. 1*a*.

First, uniform ionic crosslink networks were formed between the alginate macromers and $Ca^{2+}$. Then, the second crosslink networks were formed by photopolymerization of the methacrylate groups of the alginate and heparin in the ionically crosslinked heparin-containing alginate hydrogels through photomasks, which created micropatterns of photocrosslinked regions. Unreacted methacrylated heparin was removed from the single-crosslinked regions of the micropatterned dual-crosslinked hydrogel by incubating in media. To minimize any potential mechanical property differences between the single- and dual-crosslinked regions on encapsulated cell behavior, micropatterned dual-crosslinked hydrogels were then further photocrosslinked under UV light without a photomask to crosslink the methacrylate groups of alginate in the originally single-crosslinked regions (FIG. 6). To visualize the heparin micropatterns in the hydrogel disks, 3D heparin-micropatterned, dual-crosslinked hydrogels were stained with Toluidine Blue O. A dual-crosslinked hydrogel containing methacrylated heparin formed without the use of a photomask [FIG. 1(B), left and (C)] was stained entirely by Toluidine Blue O, indicating that heparin was coupled uniformly to the hydrogel. In contrast, Toluidine Blue O was not observed in a dual-crosslinked hydrogel formed without heparin [FIG. 1(B), right]. Importantly, when a photomask with 250 µm wide stripes was used, stripe patterns were visually confirmed in the 3D heparin-micropatterned, dual-crosslinked alginate hydrogel [FIG. 1(B), middle and (D)]. To illustrate the versatility of this micropatterning approach, grid-shaped micropatterns (200 µm) were also fabricated [FIG. 1E]. Since this simple but robust method provides precise control over 3D heparin micropatterns, this system could be a useful platform to investigate the effects of micropatterned growth factors that have a binding affinity with heparin on the behaviors of stem cells, such as adipose tissue-derived stem cells, MSCs, induced pluripotent stem cells, and embryonic stem cells.

To demonstrate that micropatterned heparin in dual-crosslinked alginate hydrogels could create 3D growth factor micropatterns, VEGF was incorporated into the constructs and detected via immunostaining to verify successful micropatterning. VEGF could be 3D micropatterned in the hydrogels with various dimensions and geometries as shown in FIG. 2. Since VEGF induces neovascularization and angiogenesis as well as supports cell survival and differentiation, this heparin-micropatterned dual-crosslinked alginate hydrogel system can provide a useful platform to regulate capillary morphogenesis and promote spatially regulated blood vessel formation in various tissue engineering applications.

While 3D micropatterned material presentation of cell adhesion ligands, mechanical properties and topographical features have been shown to have the capacity to spatially control cell behavior, the capacity to regulate encapsulated cell function by growth factor micropatterning within biomaterials has not yet been demonstrated. To evaluate whether micropatterned growth factors in this system remained bioactive and could modulate cell behavior with spatial fidelity, human MSCs (hMSCs) were photoencapsulated within 3D FGF-2 micropatterned, dual-crosslinked alginate hydrogels. FGF-2 is a mitogen for hMSCs. Cellular morphology of hMSCs varied between the FGF-2 immobilized and the non-immobilized regions. hMSCs photoencapsulated in the FGF-2 immobilized regions grew into cell clusters, while hMSCs encapsulated in the FGF-2 non-immobilized regions remained predominantly isolated through 28 days (FIGS. 2D and E). 3D clustering of cells better mimic development and healing of some tissues such as bone, cartilage and vasculature, and cannot be replicated in conventional 2D culture. In this study, micropatterned FGF-2 in the dual-crosslinked heparin/alginate hydrogels yielded relatively uniform hMSC clusters within 3D hydrogels, which scaled in size with micropattern dimensions with high cell viability throughout both micropatterns (FIG. 2D and E). This is a straightforward strategy for inducing the formation of development-mimetic cellular clusters of defined geometries in specific spatial locations within 3D hydrogels via local patterning of growth factor.

To investigate the effect of micropatterned growth factor on encapsulated stem cell differentiation, hMSCs seeded within 3D BMP-2 micropatterned, dual-crosslinked heparin/alginate hydrogels were cultured in osteogenic differentiation media for 28 days. BMP-2 is a strong osteoinductive cytokine. When the proliferation of encapsulated hMSCs in the hydrogels was examined by DNA content as a function of culture time, the DNA content significantly increased over 14 days (FIG. 7A). There was no significant difference in DNA content among any of the groups. hMSC/hydrogel constructs were evaluated for hMSC osteogenic differentiation by measuring alkaline phosphatase (ALP) activity, an early osteogenic differentiation marker. The ALP activity of encapsulated hMSCs normalized to DNA in the dual-crosslinked BMP-2 incorporated group without a micropattern was significantly higher at early time points (day 7 and 14) compared to the other groups, however, there were no significant differences between groups at the later time point (day 28,FIG. 3A). In addition, total ALP content significantly increased in all groups up to day 14, and, importantly, was greatest in the Dual_No Pattern group, followed by the Dual_Micropattern group (FIG. 7B). Since the critical late-stage marker of osteogenic differentiation is mineralization, calcium deposition was then quantified. Calcium deposition of all groups significantly increased up to 28 days (FIG. 3B and FIG. 7C). Calcium content normalized to DNA and total calcium content of the BMP-2-laden groups (Dual_Micropattern and Dual_No Pattern) were significantly higher than that of Control at days 14 and 28. Dual_No Pattern group exhibited the highest calcium content at all time points. As shown in FIG. 1b (left), heparin was immobilized throughout a dual-crosslinked hydrogel without micropatterning (Dual_No Pattern). Therefore, it is likely that more BMP-2 was immobilized in Dual_No Pattern group compared to Dual_Micropattern group. Retention of BMP-2 in dual-crosslinked heparin/alginate hydrogels accelerated both early (ALP) and late (Calcium) osteogenic differentiation, and the increased rate and extent of differentiation was even more pronounced for the Dual_No Pattern group because more BMP-2 is retained compared to Control and Dual_Micropattern groups.

As discussed earlier, this technique provides precise control over 3D growth factor micropatterning. To demonstrate the capacity to spatially localize hMSC mineralization, hMSCs were encapsulated and osteogenically differentiated within various sizes and shapes of BMP-2 micropatterned within dual-crosslinked heparin/alginate hydrogels. While, Dual_No Pattern group exhibited intense mineralization throughout whole hydrogel (FIG. 3C), as shown in FIGS. 3D-G, BMP-2 micropatterns dictated the spatial location of hMSC mineralization.

Spatiotemporal control over the presentation of bioactive factors within biomaterials may be critical for partially recapitulating multifaceted and intricate developmental and regenerative processes to drive the engineering of complex tissues. Although there has been a great deal of interest in micropatterning of bioactive molecules within 3D biomaterials, to the best of our knowledge, this is the first report of a system capable of presenting 3D patterned growth factors within a biomaterial to encapsulated stem cells, and eliciting location specific control over cellular function, such as clustering and differentiation.

In this example, we have engineered 3D growth factor-micropatterned hydrogels with various geometries and micropattern sizes by utilizing heparin's ability to immobilize growth factors. hMSCs encapsulated within growth factor-micropatterned hydrogels exhibited spatially localized growth and osteogenic differentiation responses corresponding to specific growth factor patterns. This system offers great potential for investigating the role of micropatterned growth factors on cell behavior and spatially controlling the formation of complex tissues.

Methods

Synthesis of OMAs and Methacrylated Heparin

The oxidized alginate (OA) was prepared by reacting sodium alginate (Protanal LF 200S, FMC Biopolymer) with sodium periodate (Sigma) using a modification of a previously described method. Briefly, sodium alginate (10 g) was dissolved in ultrapure deionized water ($diH_2O$, 900 ml) overnight. Sodium periodate (0.5 g) was dissolved in 100 ml $diH_2O$ and added to alginate solution under stirring in the dark at room temperature (RT) for 24 hrs. The oxidized, methacrylated alginate (OMA) macromer was prepared by reacting OA with 2-aminoethyl methacrylate (AEMA, Polysciences Inc.). To synthesize OMA, 2-morpholinoethanesulfonic acid (MES, 19.52 g, Sigma) and NaCl (17.53 g) were directly added to an OA solution (1 L) and the pH was adjusted to 6.5. N-hydroxysuccinimide (NHS, 2.12 g; Sigma) and 1-ethyl-3-(3-dimethylaminopropyl)-carbodiimide hydrochloride (EDC, 7.00 g; Sigma) (molar ratio of NHS:EDC=1:2) were added to the mixture to activate 20% of the carboxylic acid groups of the alginate. After 5 min, AEMA (3.04 g) (molar ratio of NHS:EDC:AEMA=1:2:1) was added to the product, and the reaction was maintained in the dark at RT for 24 hrs. The reaction mixture was precipitated with the addition of excess of acetone, dried in a fume hood, and rehydrated to a 1% w/v solution in $diH_2O$ for further purification. The OMA was purified by dialysis against $diH_2O$ (MWCO 3500; Spectrum Laboratories Inc.) for 3 days, treated with activated charcoal (5 g/L, 50-200 mesh, Fisher, Pittsburgh, Pa.) for 30 min, filtered (0.22 µm filter) and lyophilized. To determine the levels of alginate oxidation and methacrylation, the OMA was dissolved in deuterium oxide ($D_2O$, Sigma) to 2 w/v %, and the $^1$H-NMR spectrum was recorded on a Varian Unity-300 (300 MHz) NMR spectrometer (Varian Inc.) using 3-(trimethylsilyl) propionic acid-$d_4$ sodium salt (0.05 w/v %) as an internal standard.

The methacrylated heparin was prepared by reacting heparin (Mw 17,000, Sigma) with AEMA. Heparin (5 g) was dissolved in 50 mM MES buffer solution (1% w/v, pH 6.5) containing 0.5 M NaCl. NHS (69.0 mg) and EDC (225.5 mg) (molar ratio of NHS:EDC=1:2) were added to the solution to activate the carboxylic acid groups of the heparin. After 5 min, AEMA (108.5 mg) (molar ratio of NHS:EDC:AEMA=1:2:1) was added to the product and the reaction was maintained at RT for 24 hours. The mixture was precipitated with the addition of excess acetone, dried in a fume hood, and rehydrated to a 1% w/v solution in $diH_2O$ for further purification. The methacrylated heparin was purified by dialysis (MWCO 3500) against $diH_2O$ for 3 days, filtered (0.22 µm filter), and lyophilized. To verify the methacrylation of heparin, methacrylated heparin was dissolved in $D_2O$ and placed in a NMR tube, and the $^1$H-NMR spectrum of the sample was recorded as described above.

Microfabrication of Heparin Micropatterned Hydrogels

OMA (36 mg), alginate (Protanal LF 20/40, 9 mg) and methacrylated heparin (5 mg) were dissolved in 1 ml Dulbecco's Modified Eagle Medium (DMEM, Sigma, St. Louis, Mo.) with 0.05 w/v % photoinitiator (2-hydroxy-4'-(2-hydroxyethoxy)-2-methylpropiophenone, Sigma) at pH 7.4. Alginate macromer solution (1 ml) and aqueous slurry of calcium sulfate (40 µl; 0.21 g/ml in $diH_2O$) were separately loaded into two 1 ml syringes. After the two syringes were connected together with a female-female luer lock coupler (Value Plastics), the two solutions were mixed, immediately placed between quartz (top) and glass (bottom) plates separated by 0.4 mm spacers, and allowed to form an ionically crosslinked hydrogel at room temperature for 30 min. Subsequently, a photomask with various patterns was placed on top of the quartz plate, and a micropatterned dual-crosslinked hydrogel formed by exposure to UV light (320-500 nm, EXFO OmniCure S1000-1B, Lumen Dynamics Group) at ~20 mW/$cm^2$ through the photomask for 1 min. The unreacted methacrylated heparin from the micropatterned hydrogel was removed by washing the hydrogel in DMEM containing 0.05 w/v % photoinitiator for 1 hr, and then the micropatterned hydrogel was further stabilized by applying UV light at ~20 mW/$cm^2$ for 1 min. To the visualize spatial distribution of the methacrylated heparin in the micropatterned hydrogels, toluidine blue O staining was performed as previously reported. [3]Stained heparin in the micropatterned hydrogels was visualized using a microscope (Leitz Laborlux S, Leica) equipped with a digital camera (Coolpix 995, Nikon) and a digital camera (iPhone 5, Apple).

Fabrication of Growth Factor Micropatterned Hydrogels

Macromer solution was prepared as described earlier. To fabricate vascular endothelial growth factor (VEGF) micropatterned hydrogels, 1 µg VEGF (R&D Systems Inc.) was added to 1 ml of macromer solution, and then micropatterned dual-crosslinked hydrogels were formed as described above. The unreacted methacrylated heparin and VEGF from the micropatterned hydrogels were removed by incubating in Dulbecco's phosphate-buffered saline (DPBS, Thermo Fisher Scientific) containing calcium and magnesium with 0.05 w/v % photoinitiator for 24 hrs, and then they were further crosslinked by applying UV light at ~20 mW/$cm^2$ for 1 min. VEGF micropatterned hydrogels were fixed with 4% paraformaldehyde for 40 min and blocked with 1% BSA in PBS for 1 hr. For immunostaining of VEGF, samples were incubated in rabbit anti-human VEGF polyclonal primary antibody (Abcam) for 2 hrs at RT, followed by incubation with rhodamine-conjugated goat anti-rabbit IgG secondary antibody (Invitrogen) for 2 hrs at RT. The VEGF micropatterning in dual-crosslinked hydrogels was visualized using a fluorescence microscope (ECLIPSE TE 300, Nikon) equipped with a digital camera (Retiga-SRV, Qimaging).

Mechanical Testing

The elastic moduli of the hydrogels were determined by performing uniaxial, unconfined constant strain rate compression tests at room temperature using a constant crosshead speed of 1%/sec on a mechanical testing machine (1 lbs Actuator, TestResources) equipped with a 5 N load cell. Elastic moduli were calculated from the first non-zero linear slope of the stress versus strain plots within 5% strain (N=3).

Fabrication of Cell-Laden Growth Factor Micropatterned Hydrogels

To isolate hMSCs, bone marrow aspirates were obtained from the posterior iliac crest of healthy donors under a protocol approved by the University Hospitals of Cleveland Institutional Review Board and processed as previously described. Briefly, the bone marrow aspirates were washed with growth medium comprised of low-glucose DMEM (DMEM-LG) with 10% prescreened fetal bovine serum (FBS, Gibco). Mononuclear cells were isolated by centrifugation in a Percoll (Sigma) density gradient and the isolated mononuclear cells were plated at $1.8\times10^5$ cells/$cm^2$ in DMEM-LG containing 10% FBS and 1% penicillin/streptomycin (P/S, Thermo Fisher Scientific) in an incubator at 37° C. and 5% $CO_2$. After 4 days of incubation, non-adherent cells were removed and adherent cell were maintained in DMEM-LG containing 10% FBS and 1% P/S with media changes every 3 days. After 14 days of culture, the cells were passaged at a density of $5\times10^3$ cells/$cm^2$. Primary hMSCs were further expanded in media containing DMEM- LG, 10% FBS (Sigma), 1% P/S and 10 ng/ml fibroblast growth factor-2 (FGF-2, R&D System Inc.) with media changes every 3 days. To fabricate hMSC-encapsulated FGF-2 micropatterned hydrogels, 1 µg FGF-2 was added to 1 ml of hMSC (passage number 3, $1 \times 10^6$ cells/ml) suspended macromer solution with 0.05% w/v photoinitiator, and then micropatterned dual-crosslinked hydrogels were formed as described above. The unreacted methacrylated heparin and FGF-2 from the micropatterned hydrogel was removed by incubating the hydrogel in DMEM containing 10% FBS and 1% P/S with 0.05 w/v % photoinitiator in a humidified incubator at 37° C. with 5% $CO_2$ for 24 hrs, and then the micropatterned hydrogel was further crosslinked by applying UV light at 20 mW/cm$^2$ for 1 min. Hydrogel-cell construct disks were created using an 8 mm diameter biopsy punch, placed in wells of 24-well tissue culture plates with 1 ml DMEM containing 10% FBS and 1 P/S, and cultured in a humidified incubator at 37° C. with 5% $CO_2$ for 28 days with media changes every 3 days. hMSCs encapsulated in dual-crosslinked hydrogels with micropatterned heparin grids (200 µm) without FGF-2 were prepared as a control group. The viability of encapsulated hMSCs in the FGF-2 micropatterned, dual-crosslinked hydrogels was investigated using a Live/Dead assay comprised of fluorescein diacetate (FDA, 1.5 mg/ml in dimethyl sulfoxide, Sigma) and ethidium bromide (EB, 1 mg/ml in PBS, Thermo Fisher Scientific). The staining solution was freshly prepared by mixing 100 µl FDA solution and 50 µl EB solution with 30 µl PBS (pH 8). At predetermined time points, 20 µl of staining solution was added into each well and incubated for 3-5 min at RT, and then stained hydrogel-cell constructs were imaged using a fluorescence microscope (ECLIPSE TE 300) equipped with a digital camera (Retiga-SRV).

hMSCs were also encapsulated in BMP-2 micropatterned dual-crosslinked hydrogels to evaluate the spatial regulation of osteogenic differentiation of stem cells in this system. 50 µg of BMP-2 was added to 1 ml of hMSC ($5 \times 10^6$ cells/ml) suspended macromer solution, and then dual-crosslinked hydrogels without and with micropatterning were formed as described above. The unreacted methacrylated heparin and BMP-2 from the micropatterned hydrogel was removed by incubating the hydrogel in DMEM containing 10% FBS and 1% P/S with 0.05 w/v % photoinitiator in a humidified incubator at 37° C. with 5% $CO_2$ for 24 hrs, and then the micropatterned hydrogel was further crosslinked by applying UV light at 20 mW/cm$^2$ for 1 min. Photocrosslinked hydrogel-cell construct disks were created using an 8 mm diameter biopsy punch, placed in wells of 24-well tissue culture plates with 1 ml osteogenic media [10 mM β-glycerophosphate (CalBiochem), 50 µM ascorbic acid (Wako), and 100 nM dexamethasone (MP Biomedicals)] containing 10% FBS and 1% P/S, and cultured in a humidified incubator at 37° C. with 5% $CO_2$ for 28 days with media changes every 3 days.

To determine the extent of hMSC osteogenic differentiation when cultured in BMP-2 micropatterned dual-crosslinked hydrogels, at predetermined time points each hydrogel-cell construct was removed from the 24-well plates, put in 1 ml ALP lysis buffer and homogenized at 35,000 rpm for 30 s using a TH homogenizer (Omni International) on ice. The homogenized solutions were centrifuged at 500 g with a Sorvall Legend RT Plus Centrifuge (Thermo Fisher Scientific). The supernatants were collected for DNA, ALP, and calcium analysis (N=6). DNA content in the supernatant was also measured using a Picogreen® assay kit (Invitrogen) according to the manufacturer's instructions. Fluorescence intensity of the dye-conjugated DNA solution was measured using a fluorescence microplate reader (FMAX, Molecular Devices) set at 485 nm excitation and 538 nm emission. For ALP measurement, supernatant (100 µl) was treated with p-nitrophenylphosphate ALP substrate (pNPP, 100 µl, Sigma) at 37° C. for 30 min, and then 0.1 N NaOH (50 µl) was added to stop the reaction. The absorbance was measured at 405 nm using a plate reader (VersaMax). To measure calcium content, an equal volume of 1.2 N HCl was added into each remaining lysate solution and pellet, the mixed solutions were centrifuged at 500 g with a centrifuge (Thermo Fisher Scientific). A calcium assay was then performed using a kit (Pointe Scientific) according to the manufacturer's instructions. Briefly, supernatant (4 µl) was mixed with a color and buffer reagent mixture (250 µl) and the absorbance was read at 570 nm on a microplate reader (VersaMax). All ALP and calcium content measurements were normalized to DNA content. To visualize the calcium deposition in the hydrogel disks, hydrogel-cell constructs were fixed with 4% paraformaldehyde for 40 min, stained with Alizarin Red S (2 w/v %, pH 4.2; Sigma) for 5 min, and imaged using a microscope (Leitz Laborlux S, Leica) equipped with a digital camera (Coolpix 995, Nikon).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method for forming a spatially patterned biodegradable hydrogel having discrete portions and/or patterns of immobilized bioactive agent, the method comprising:
    a) combining (i) aoxidized, methacrylated natural polymer macromers, which include at least one first photocrosslinkable group; (ii) bioactive agent-coupling polymer macromers, which include at least one second photocrosslinkable group reactive with the first crosslinkable group; (iii) at least one bioactive agent that couples to the bioactive agent coupling natural polymer macromers; and (iv) at least one cell;
    b) crosslinking the oxidized, methacrylated natural polymer macromers to form a photocrosslinkable hydrogel that includes photocrosslinkable base polymer, the bioactive agent-coupling polymer macromers, the at least one bioactive agent, and the at least one cell encapsulated in the photocrosslinkable hydrogel;
    c) selectively exposing discrete portions of the photocrosslinkable hydrogel to actinic radiation effective to initiate cross-linking of the photocrosslinkable base polymer and the bioactive agent-coupling polymer macromers at the exposed portions to provide the hydrogel with discrete portions and/or patterns of immobilized bioactive agent;
    d) removing bioactive agent-coupling polymer macromers that are not crosslinked with the base polymer and optionally, bioactive agent that is not coupled to the crosslinked bioactive agent-coupling polymer macromers; and
    e) further exposing the hydrogel to actinic radiation effective to initiate cross-linking of the methacrylate groups of the base polymer in regions of the hydrogel not previously exposed to actinic radiation;
    wherein the discrete portions and/or patterns of immobilized bioactive agent modulate a function and/or characteristic of the at least one cell encapsulated therein and elicit location specific control over cellular function.

2. The method of claim 1, wherein the photocrosslinkable hydrogel includes a photoinitiator.

3. The method of claim 1, wherein selectively exposing the discrete portions of the photocrosslinkable hydrogel to the actinic radiation comprises providing a photomask with a defined pattern and using the photomask to selectively expose the discrete portions of the photocrosslinkable hydrogel to the actinic radiation.

4. The method of claim 1, wherein the oxidized, methacrylated, natural polymer macromers are polysaccharides, which are oxidized to aldehyde saccharide units.

5. The method of claim 1, wherein the oxidized, methacrylated natural polymer macromers are ionically crosslinkable.

6. The method of claim 1, wherein the bioactive agent is non-covalently coupled to the crosslinked bioactive agent-coupling polymer macromers.

7. The method of claim 1, wherein the bioactive agent coupling-polymer macromers are acrylated and/or methacrylated polymer macromers.

8. The method of claim 7, wherein the acrylated and/or methacrylated polymer macromers comprise acrylated and/or methacrylated heparin.

9. The method of claim 8, wherein the bioactive agent is a heparin binding growth factor.

10. The method of claim 9, wherein the heparin binding growth factor comprises at least one of FGF, VEGF, TGF-β, or BMP.

11. A method for forming a spatially patterned biodegradable hydrogel having discrete and/or local patterns of immobilized growth factor, the method comprising:
  combining (i) aoxidized, methacrylated alginate; (ii) acrylated and/or methacrylated heparin; (iii) heparin binding growth factor; and (iv) cells;
  crosslinking oxidized, methacrylated alginate to form a photocrosslinkable oxidized, methacrylated alginate hydrogel;
  selectively photocrosslinking acrylated and/or methacrylated heparin with the oxidized, methacrylated alginate hydrogel in the presence of the heparin binding growth factor and cells to create discrete and/or local patterns of photocrosslinked regions of heparin crosslinked to the alginate hydrogel; wherein the cells are encapsulated within the alginate hydrogel;
  removing unreacted acrylated and/or methacrylated heparin and heparin binding growth factor not bound to crosslinked heparin; and
  further photocrosslinking the oxidized, methacrylated alginate hydrogel to photocrosslink methacrylate groups of the oxidized, methacrylated alginate hydrogel in regions of the hydrogel not previously photocrosslinked;
  wherein the discrete and/or local patterns of photocrosslinked regions include immobilized heparin binding growth factor that modulates a function and/or characteristic of the cells encapsulated therein and elicits location specific control over cellular function.

12. The method of claim 11, wherein the heparin binding growth factor comprises at least one of FGF, VEGF, TGF-β, or BMP.

* * * * *